(12) United States Patent
Kuchler

(10) Patent No.: US 8,355,881 B2
(45) Date of Patent: Jan. 15, 2013

(54) DEVICE AND PROCESS FOR MACHINE DIAGNOSTICS BY MEANS OF VIBRATION MEASUREMENT

(75) Inventor: Alexander Kuchler, Unterschleissheim (DE)

(73) Assignee: Prüftechnik Dieter Busch AG, Ismaning (DE)

( * ) Notice: Subject to any disclaimer, the term of this patent is extended or adjusted under 35 U.S.C. 154(b) by 365 days.

(21) Appl. No.: 12/539,706

(22) Filed: Aug. 12, 2009

(65) Prior Publication Data
US 2010/0042343 A1 Feb. 18, 2010

(30) Foreign Application Priority Data
Aug. 12, 2008 (DE) .......................... 10 2008 038 690

(51) Int. Cl.
*G01H 1/00* (2006.01)
(52) U.S. Cl. .............................. 702/56; 702/77; 702/183
(58) Field of Classification Search .................... 702/39, 702/56, 76, 77, 189, 190, 182, 183
See application file for complete search history.

(56) References Cited

U.S. PATENT DOCUMENTS

| 5,633,811 | A | * | 5/1997 | Canada et al. .................. 702/56 |
| 5,936,561 | A | * | 8/1999 | Lee ............................... 341/143 |
| 6,507,790 | B1 | | 1/2003 | Radomski |
| 7,424,403 | B2 | * | 9/2008 | Robinson et al. ............. 702/189 |

* cited by examiner

*Primary Examiner* — Manuel L Barbee
(74) *Attorney, Agent, or Firm* — Roberts Mlotkowski Safran & Cole, P.C.; David S. Safran

(57) ABSTRACT

A device for machine diagnostics, with a vibration sensor (12) for detecting vibration signals on the machine (10), a unit (14) for conditioning the vibration signals, an A/D converter (16) for digitizing the conditioned vibration signals, a data processing unit (20) for splitting the digital signals into at least two frequency ranges, the data processing unit being made to scale the signal for each frequency range to an amplitude resolution which is less than the amplitude resolution of the A/D converter, and an evaluation unit (30) for further evaluation of the split signals.

13 Claims, 1 Drawing Sheet

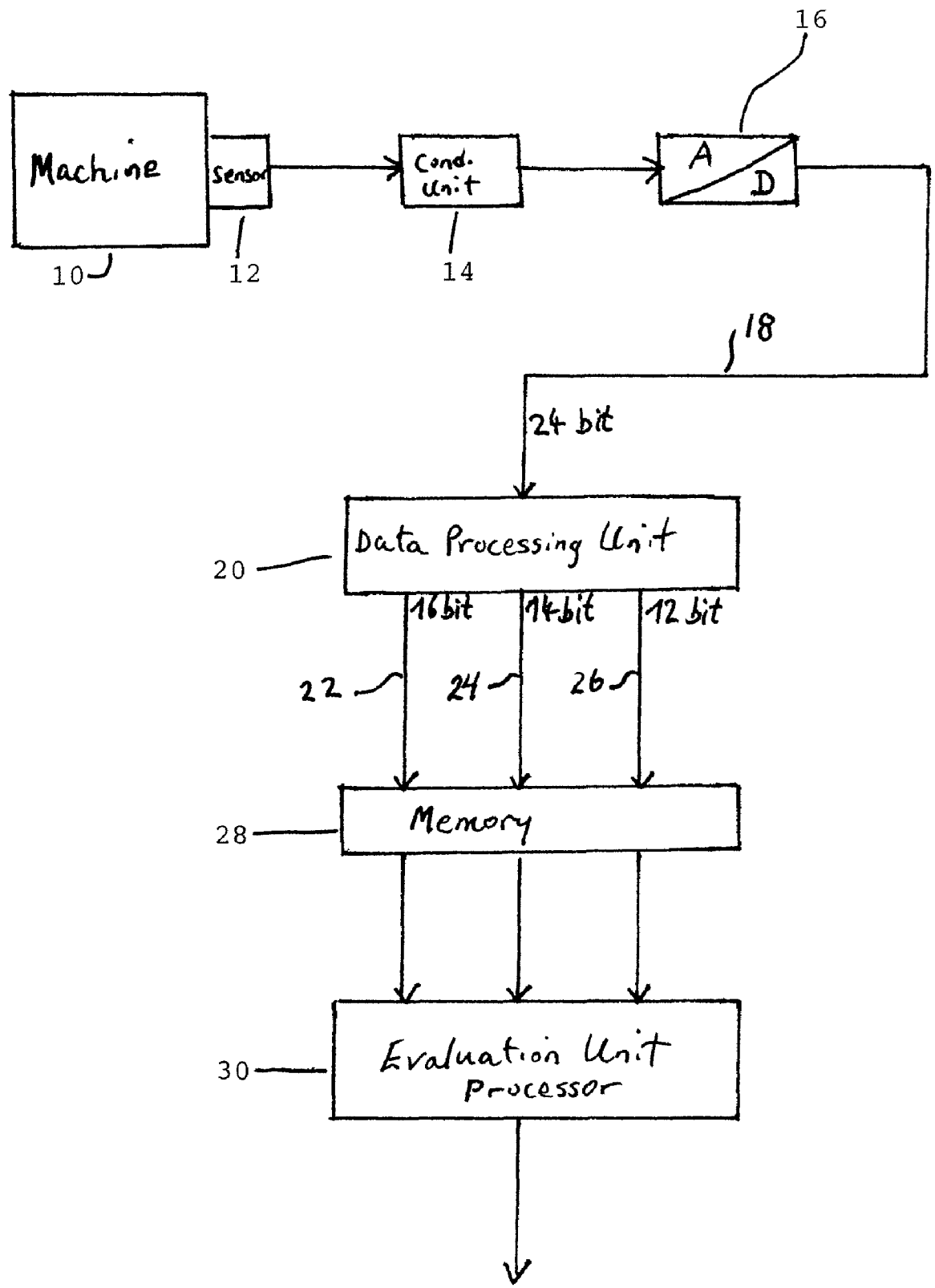

DEVICE AND PROCESS FOR MACHINE DIAGNOSTICS BY MEANS OF VIBRATION MEASUREMENT

BACKGROUND OF THE INVENTION

1. Field of Invention

This invention relates to a device and a process for machine diagnostics, by means of a vibration sensor vibration signals on the machine being detected and then being digitally processed.

2. Description of Related Art

In typical applications in machine diagnostics and maintenance, both signal portions in the high and also in the low frequency range must be examined. Since for the same measured quantity (acceleration, velocity, path), different frequency ranges with very different amplitudes occur, the signal is conventionally divided first into different frequency ranges and filtered accordingly, and then, amplified such that the signal of the respective frequency range triggers the analog-digital converter (ADC) as optimally as possible. Signal detection itself can take place either in parallel with several signal paths and ADCs or serially in succession by switching different analog channels to an individual ADC.

One possibility for reducing the number of required ADCs with a uniform measurement time is the use of a higher resolution ADC. This approach is described, for example, in U.S. Pat. No. 5,633,811 where a sigma-delta ADC is used for digitization. Furthermore, U.S. Pat. No. 5,633,811 also gives an example for a slow and a fast ADC being able to be switched in parallel in order to provide for optimized digitization into different frequency ranges. Other examples for use of sigma-delta ADCs for vibration analysis of machines can be found in U.S. Pat. No. 6,507,790 B1 or German Patent Application DE 10 2007 042 678 A1 corresponds to U.S. Pat. No. 7,424,403 B2.

The disadvantage in the use of a high resolution ADC is that the amount of data formed according to the high ADC resolution is very large, and thus, makes further processing of the digitized signal more difficult.

SUMMARY OF THE INVENTION

A primary object of this invention is to devise a device for machine diagnostics by means of vibration analysis which provides for optimized digital signal evaluation.

It is a further object of the invention to provide for a corresponding process.

These objects are achieved by a device as and a process as described below.

In the approach in accordance with the invention, it is advantageous that, because there is a data processing unit for splitting the digital signals into at least two frequency ranges, which is made for each frequency range to scale the signal to an amplitude resolution which is less than the amplitude resolution of the ADC, further processing of the digital vibration measurement data is reduced as a result of the reduced amplitude resolution without a loss of accuracy occurring, since the high resolution bandwidth of the ADC can no longer be used at all after digital frequency splitting and generally lower resolution is sufficient.

Preferred configurations of the invention will become apparent from the following description in conjunction with the accompanying drawings.

BRIEF DESCRIPTION OF THE DRAWINGS

The sole FIGURE is a block diagram of the data processing of one example of a machine diagnostics device in accordance with an embodiment of the invention.

DETAILED DESCRIPTION OF THE INVENTION

According to the sole FIGURE, the illustrated example of a device for machine diagnostics in accordance with the invention has a vibration sensor 12 for detecting vibration signals on a machine 10, the vibration signals being analog-conditioned in a unit 14 in the manner necessary for the following ADC. Typically the conditioning unit 14 comprises anti-aliasing filters (low pass filter) and a variable amplifier in order to effectively control the ADC 16.

The conditioned signals are broadband-digitized by the ADC 16 and transferred as a continuous, high-resolution data stream 18 to the data processing unit 20. Preferably, the ADC 16 has a sampling rate of at least 100 kHz and an amplitude resolution of at least 18 bits. Preferably, the ADC is implemented in sigma-delta technology.

The data processing unit 20 is made to split the broadband signal 18 into several frequency ranges (in this example, three frequency ranges) and to scale the signal in each frequency range to an amplitude resolution which is less than the amplitude resolution of the ADC 16. Preferably, the amplitude resolution for each of the frequency ranges is at least 2 bits less than the resolution of the A/D converter. In the illustrated example, the amplitude resolution of the ADC 16, and thus, the width of the data stream is 18 is 24 bits, while the resolution and width of the three frequency-split streams 22, 24, 26 is 16, 14 and 12 bits, respectively. Preferably, the amplitude resolution for each of the frequency ranges is a maximum of 16 bits.

The frequency-split signals 22, 24, 26 are stored in a memory 28 and transferred from there to a processor 30 which is used as an evaluation unit for further evaluation. In this example, the data processing unit 20 and the processor 30 are implemented as separate modules which each are connected by DMA (direct memory access) to the memory 28. But fundamentally, the data processing unit 20, the memory 28 and the processor 30 could also be implemented in the same module.

The data processing unit 20 can be implemented, for example, as a FPGA (field programmable gate array), a CPLD (complex programmable logic device), a DSP (digital signal processor) or as a system processor.

It goes without saying that the diagnostic device can be made with several channels, then, for each input, preferably, a separate conditioning unit 14, a separate ADC 16 and a separate data processing unit 20 being provided.

As one version the processor 30 can be made as a DSP in addition to the system processor and can assume signal processing and then transfer either further filtered and/or in some other way modified signals or also computed final results for storage and/or display to the system processor.

This invention offers the following advantages: signal streams with well controlled signal levels in different frequency ranges can be obtained; several signal streams in different frequency ranges can be obtained in parallel; the amount of data which is formed is reduced to the required degree; repeated execution of analog signal conditioning can be avoided; use of several ADCs can be avoided.

What is claimed is:

1. Device for machine diagnostics, comprising
a vibration sensor for detecting vibration on a machine and outputting vibration signals representative of vibration detected,
a conditioning unit for conditioning the vibration signals,
an A/D converter for digitizing the conditioned vibration signals,
a data processing unit directly connected to the A/D converter for splitting the digitized signals received directly from the A/D converter into parallel split signals for at least two different frequency ranges, the data processing unit being adapted for scaling the signal for each of the different frequency ranges to an amplitude resolution which is less than the amplitude resolution of the digitized signals produced by the A/D converter, and
an evaluation unit receiving the parallel split signals for evaluation and modification.

2. Device in accordance with claim 1, wherein the A/D converter has a sampling rate of at least 100 kHz.

3. Device in accordance with claim 1, wherein the A/D converter has an amplitude resolution of at least 18 bits.

4. Device in accordance with claim 3, wherein the amplitude resolution for each of the frequency ranges is a maximum 16 bits.

5. Device in accordance with claim 1, wherein the A/D converter comprises sigma-delta technology.

6. Device in accordance with claim 1, wherein the data processing unit and the evaluation unit are separate modules, each of which is connected to a memory by direct memory access via which the signals are transferred.

7. Device in accordance with claim 1, comprising a plurality of input channels, each input channel being provided with a respective conditioning unit, A/D converter and data processing unit for frequency splitting.

8. Device in accordance with claim 1, wherein each of the frequency ranges has an amplitude resolution that is at least 2 bits less than the resolution of the digitized signals produced by the A/D converter.

9. Device in accordance with claim 1, wherein the data processing unit is adapted for splitting the signals prior to performing any data processing of the digitized signals.

10. Device in accordance with claim 1, wherein the data processing unit is adapted to at least one of further filter and otherwise modified the split digital signals.

11. Process for machine diagnostics, comprising the steps of:
detecting vibration on a machine by means of a vibration sensor which produces vibration signals representative of vibration detected,
conditioning the vibration signals,
digitizing the conditioned vibration signals by means of an A/D converter,
splitting the digitized signals into parallel split signals for at least two different frequency ranges by means of a data processing unit that is directly connected to the A/D converter, and for each frequency range, the signal being scaled to an amplitude resolution which is less than the amplitude resolution of the digitized signals produced by the A/D converter, and
transferring the parallel split signals to an evaluation unit for evaluation and modification.

12. Process according to claim 11, wherein the data processing unit and the evaluation unit are separate modules, each of which is connected to a memory, wherein signals are transferred between the memory and each of the data processing unit and the evaluation unit by direct memory access.

13. Process according to claim 11, wherein the data processing performed on the split signals comprises Fourier Transform processing.

* * * * *